(12) United States Patent
Ali et al.

(10) Patent No.: US 7,326,529 B2
(45) Date of Patent: Feb. 5, 2008

(54) METHOD OF DIAGNOSING, MONITORING, STAGING, IMAGING AND TREATING PROSTATE CANCER

(75) Inventors: Shujath Ali, Santa Clara, CA (US); Robert Cafferkey, San Jose, CA (US); Herve Recipon, San Francisco, CA (US); Yongming Sun, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 569 days.

(21) Appl. No.: 10/431,842

(22) Filed: May 8, 2003

(65) Prior Publication Data

US 2003/0194739 A1 Oct. 16, 2003

Related U.S. Application Data

(62) Division of application No. 09/730,018, filed on Dec. 4, 2000, now abandoned.

(60) Provisional application No. 60/169,083, filed on Dec. 6, 1999.

(51) Int. Cl.
*C12Q 1/68* (2006.01)
*G01N 33/574* (2006.01)

(52) U.S. Cl. .............................................. 435/6; 435/7

(58) Field of Classification Search ...................... None
See application file for complete search history.

(56) References Cited

U.S. PATENT DOCUMENTS

| | | | |
|---|---|---|---|
| 4,690,914 A | 9/1987 | Callut et al. ................ | 502/400 |
| 5,585,103 A | 12/1996 | Raychaudhuri ........... | 424/278.1 |
| 5,756,309 A * | 5/1998 | Soppet et al. .............. | 435/69.1 |
| 5,882,864 A | 3/1999 | An et al. ........................ | 435/6 |
| 5,948,890 A | 9/1999 | Soppet et al. | |
| 5,985,270 A | 11/1999 | Srivastava ............... | 424/93.71 |
| 6,183,968 B1 | 2/2001 | Bandman et al. | |
| 2005/0037379 A1* | 2/2005 | Billing-Medel et al. ....... | 435/6 |

FOREIGN PATENT DOCUMENTS

| | | |
|---|---|---|
| EP | 1033401 A2 | 9/2000 |
| JP | EP 0 679 716 A1 | 11/1994 |
| WO | WO 95/14772 A1 | 6/1995 |
| WO | WO 96/39435 A1 | 12/1996 |
| WO | WO 99/06550 A2 | 2/1999 |
| WO | WO 99/09155 A1 | 2/1999 |
| WO | WO 99/09166 A2 | 2/1999 |
| WO | WO 99/46374 A2 | 9/1999 |
| WO | WO 99/60162 | 11/1999 |
| WO | WO 00/04149 A2 | 1/2000 |
| WO | WO 00/23111 A1 | 4/2000 |
| WO | WO 00/55174 A1 | 9/2000 |
| WO | WO 00/55350 A1 | 9/2000 |
| WO | WO 00/58494 A1 | 10/2000 |
| WO | WO 01/07476 A1 | 2/2001 |
| WO | WO 01/22920 A2 | 4/2001 |
| WO | WO 01/25272 A2 | 4/2001 |
| WO | WO 01/25273 A2 | 4/2001 |
| WO | WO 01/25434 A1 | 4/2001 |
| WO | WO 01/27158 A2 | 4/2001 |
| WO | WO 01/34802 A2 | 5/2001 |
| WO | WO 01/39798 A1 | 6/2001 |
| WO | WO 01/51633 A2 | 7/2001 |
| WO | WO 01/57272 A2 | 8/2001 |
| WO | WO 01/60860 A2 | 8/2001 |
| WO | WO 02/30268 A2 | 4/2002 |
| WO | WO 02/055735 A2 | 7/2002 |

OTHER PUBLICATIONS

Pantel, et al (Journal of Haematotherapy 5: 359-367, 1996).*
Griffin et al., "Initial Clinical Study of Indium-111-Labeled Clone 110 Anticarcinoembryonic Antigen Antibody in Patients With Colorectal Cancer", *J. Clin. Onc.* 1991 9(4) :631-640.
Lauffer R.B., "Targeted Relaxation Enhancement Agents for MRI", *Magnetic Resonance in Medicine* 1991 22:339-342.
Pastan et al., "Immunotoxins", *Cell* 1986 47:641-648.
Raming et al., "Identification of a Novel G-Protein Coupled Receptor Expressed in Distinct Brain Regions and a Defined Olfactory Zone", *Receptor Channels* 1998 6(2) :141-51.
Rosenberg S. A. et al., "Use of Tumor-Infiltrating Lymphocytes and Interleukin-2 In The Immunotherapy of Patients with Metastatic Melanoma", *N. England J. Med.* 1988 319:1676-1680.
Sumerdon et al., "An Optimized Antibody-Chelator Conjugate for Imaging of Carcinoembryonic Antigen with Indium-111", *Nucl. Med. Biol.* 1990 17:247-254.
Deguchi et al., "Detection of micrometastatic prostate cancer cells in the bone marrow of patients with prostate cancer", British Journal of Cancer 1997 75(5) :634-638.
DATABASE EMBL Database accession No. AF079864 XP002277263 Aug. 17, 1998.
DATABASE EMBL Database accession No. AI805082 XP002277262 Jul. 7, 1999.
Adams, MD. et al, Initial assessment of human gene diversity and expression patterns based upon 83 million nucleotides of cDNA sequence, Nature. 1995, vol. 377, pp. 3-174.
Bulger et al, Comparative structural and functional analysis of the olfactory receptor genes flanking the human and mouse β-globin gene clusters, PNAS, 2000, vol. 97, pp. 14560-14565.
Bussmakers, M.J. Changes in gene expression and targets for therapy. European Urology. 1999, vol. 35, No. 5-6, pp. 408-412.
Hoon et al, Melanoma patients immunized with melanoma vaccine induce antibody response to recombinant MAGE-1 antigen. Journal of Immunology. 1995, vol. 154, pp. 730-737.
Xu et al, *PSGR*, a novel prostate-specific gene with homology to a G protein-coupled receptor, is over expressed in prostate cancer, Cancer Research, 2000, vol. 60, pp. 6568-6572.

(Continued)

*Primary Examiner*—Christopher Yaen
(74) *Attorney, Agent, or Firm*—Licata & Tyrrell P.C.; Keith R. McCollum

(57) ABSTRACT

The present invention provides new markers and methods for detecting, diagnosing, monitoring, staging, prognosticating, imaging and treating prostate cancer.

5 Claims, No Drawings

OTHER PUBLICATIONS

Hla et al. An abundant transcript induced in differentiating human endothelial cell encodes a polypeptide with structural similarities to G-protein-coupled receptors. JBC. Jun. 5, 1990; vol. 265(16):9308-9313.

Ross et al. RTA, a candidate G protein-coupled receptor: cloning, sequencing, and tissue distribution. PNAC. Apr. 1990; vol. 87:3052-3056.

* cited by examiner

SEQUENCE LISTING

```
<160> NUMBER OF SEQ ID NOS: 13
<210> SEQ ID NO 1
<211> LENGTH: 310
<212> TYPE: DNA
<213> ORGANISM: Homo sapiens
<220> FEATURE:
<221> NAME/KEY: unsure
<222> LOCATION: (5)

<400> SEQUENCE: 1
atttntggaa gccagggctt gtcacagtct ctactgttat tatgcattac ctgggaattt      60
atataagccc ttaataataa taccaatgaa catctcatgt gtgctcacaa tgttctggca     120
ctattataag tgcttcacag gttttatgtg ttcttcgtaa ctttatggag taggtaccat     180
ttgtgtctct ttattataag tgagagaaat gaagtttata ttatcaaggg gactaaagtc     240
acacggcttg tgggcactgt gccaagattt aaaattaaat ttgatggttg aatacagtta     300
cttaatgacc                                                            310

<210> SEQ ID NO 2
<211> LENGTH: 2994
<212> TYPE: DNA
<213> ORGANISM: Homo sapiens

<400> SEQUENCE: 2
aatttgtaat acgactcact atagggcggc cgcgaattcg gcaccaggaa gacacagtga      60
gttagcacca ccaccaggaa ttggcctttc agctctgtgc ctgtctccag tcaggctgga     120
ataagtctcc tcatatttgc aagctcggcc ctcccctgga atctaaagcc tcctcagcct     180
tctgagtcag cctgaaagga acaggccgaa ctgctgtatg ggctctactg ccagtgtgac     240
ctcaccctct ccagtcaccc ctcctcagtt ccagctatga gttcctgcaa cttcacacat     300
gccacctttg tgcttattgg tatcccagga ttagagaaag cccatttctg ggttggcttc     360
cccctccttt ccatgtatgt agtggcaatg tttggaaact gcatcgtggt cttcatcgta     420
aggacggaac gcagcctgca cgctccgatg tacctctttc tctgcatgct tgcagccatt     480
gacctggcct tatccacatc caccatgcct aagatccttg ccctttctg gtttgattcc     540 cgagagatta gctttgaggc ctgtcttacc cagatgttct ttattcatgc cctctcagcc     600
```

-continued

```
attgaatcca ccatcctgct ggccatggcc tttgaccgtt atgtggccat ctgccaccca    660
ctgcgccatg ctgcagtgct caacaataca gtaacagccc agattggcat cgtggctgtg    720
gtccgcggat ccctcttttt tttcccactg cctctgctga tcaagcggct ggccttctgc    780
cactccaatg tcctctcgca ctcctattgt gtccaccagg atgtaatgaa gttggcctat    840
gcagacactt tgcccaatgt ggtatatggt cttactgcca ttctgctggt catgggcgtg    900
gacgtaatgt tcatctcctt gtcctatttt ctgataatac gaacggttct gcaactgcct    960
tccaagtcag agcgggccaa ggcctttgga acctgtgtgt cacacattgg tgtggtactc   1020
gccttctatg tgccacttat tggcctctca gttgtacacc gctttgggaaa cagccttcat   1080
cccattgtgc gtgttgtcat gggtgacatc tacctgctgc tgcctcctgt catcaatccc   1140
atcatctatg gtgccaaaac caaacagatc agaacgggg tgctggctat gttcaagatc   1200
agctgtgaca aggacttgca ggctgtggga ggcaagtgac ccttaacact acacttctcc   1260
ttatctttat tggcttgata acataatta tttctaacac tagcttattt ccagttgccc   1320
ataagcacat cagtactttt ctctggctgg aatagtaaac taaagtatgg tacatctacc   1380
taaaggacta ttatgtggaa aatacatac taatgaagta ttcatgatt taaagactac   1440
aataaaacca acatgctta taacattaag aaaaacaata aagatacatg attgaaacca   1500
agttgaaaaa tagcatatgc cttggaggaa atgtgctcaa attactaatg atttagtgtt   1560
gtccctactt tctctctctt ttttctttct tttttttta ttatggttag ctgtcacata   1620
caactttttt ttttttttgag atggggtctc gctctgtcac caggctggag tgcagtggcg   1680
cgatctcggc tcactgcaac ctccacatcc catgttgaag taattcttct gcctcagcct   1740
cccgagtagc tgggactaga ggaacgtgcc accatgactg gctaattttc tgtatttttt   1800
agtagagaca gagtttcacc atgttggcca ggatggtctc gatctcctga ccttgtgatc   1860
cacccgcctc agcctcccaa agtgttggga ttacaggtgt gaaccactgt gcccggcctg   1920
tgtacaactt tttaaatagg gaatatgata gcttcgcatg gtggtgtgca cctatagccc   1980
ccactgcctg gaaagctgag gcgggagaat cgcttgagtc caggagtttg aggttgcagt   2040
gatccacgat cgtaccactg cactccagcc tgggcaacag agcaagaccc tgtctcaaag   2100
cataaaatgg aataacatat caaatgaaac agggaaaatg aagctgacaa tttatggaag   2160
ccagggcttg tcacagtctc tactgttatt atgcattacc tgggaattta tataagccct   2220
taataataat gccaatgaac atctcatgtg tgctcacaat gttctggcac tattataagt   2280
gcttcacagg ttttatgtgt tcttcgtaac tttatggagt aggtaccatt tgtgtctctt   2340
tattataagt gagagaaatg aagtttatat tatcaagggg actaaagtca cacggcttgt   2400
gggcactgtg ccaagattta aaattaaatt tgatggttga atacagttac ttaatgacca   2460
tgttatattg cttcctgtgt aacatctgcc atttatttcc tcagctgtac aaatcctctg   2520
ttttctctct gttacacact aacatcaatg gctttgtact tgtgatgaga gataaccttg   2580
ccctagttgt gggcaacaca tgcagaataa tcctgtttta cagctgcctt tcgtgatctt   2640
attgcttgct ttttttccaga ttcagggaga atgttgttgt ctatttgtct cttacatctc   2700
cttgatcatg tcttcatttt ttaatgtgct ctgtacctgt caaaaatttt gaatgtacac   2760
cacatgctat tgtctgaact tgagtataag ataaaataaa attttatttt aaattttaaa   2820
aaaaaaaaaa aaaaaaaaac tcgactctag attgcggccg cggtcatagc tgtttcctga   2880
acagatcccg ggtggcatcc ctgtgacccc tccccagtgc ctctcctggc cctggaagtt   2940
gccactccag tgcccaccag ccttgtccta ataaaattaa gttgcatcat tttg   2994
```

<210> SEQ ID NO 3
<211> LENGTH: 230
<212> TYPE: DNA
<213> ORGANISM: Homo sapiens
<220> FEATURE:
<221> NAME/KEY: unsure
<222> LOCATION: (23)

<400> SEQUENCE: 3

```
ggaggctgaa acctttaggg cgntgcctgc ttgcaaggtc aggcaagctg gattctggtc    60
cccacctttg cagagagaac agcgatgttg tgcgcccatt tctcagatca aggaccggcc   120
catcttacta cctccaagag tgcttttctc tctaataaga aaacatctac tttgaaacat   180
ctactgggcg agaccaggag tgagctcagc ctgtaattct ggaatttcgg              230
```

<210> SEQ ID NO 4
<211> LENGTH: 660
<212> TYPE: DNA
<213> ORGANISM: Homo sapiens

<400> SEQUENCE: 4

```
cgtacgtaag ctcggaattc ggctcgaggg cgtgcaaaca gagcgccact gggaggctga    60
aacctttagg ccgatgcctg cttgcaaggt caggcaagct ggattctggt ccccaccttt   120
gcagagagaa cagcgatgtt gtgcgcccat ttctcagatc aaggaccggc ccatcttact   180
acctccaaga gtgctttcct ctctaataag gtaaactgat cggtgggcca agggcgttat   240
cgacggatcg ctcagtatgg tagctgcatc aggaggccct gggagagggt ctcccaggaa   300
tttgggagcc ttcagaagtt tgggaaaaca agggaagggt gagcagcagg ctttcaccga   360
taccacctgg cgggagcacc tactcgcggt tcctggagag accggcagcc gccctgggca   420
gaaagggaca agaaaatgt ttcgcagcac gcgggacctg caggacctag gcggggaga    480
ggcttgggag tgggaactag cacccgctgt aaggtctgcc ataagactta atgtttgtct   540
ccaatgggat ggagtcctgg cataagcaaa attaatattg ataacgttat tattatttaa   600
aatttgtaaa tattgtaaaa tattttagaa aacatctact ttgaaacatc tactgggcga   660
```

<210> SEQ ID NO 5
<211> LENGTH: 191
<212> TYPE: DNA
<213> ORGANISM: Homo sapiens
<220> FEATURE:
<221> NAME/KEY: unsure
<222> LOCATION: (120)
<220> FEATURE:
<221> NAME/KEY: unsure
<222> LOCATION: (121)
<220> FEATURE:
<221> NAME/KEY: unsure
<222> LOCATION: (125)
<220> FEATURE:
<221> NAME/KEY: unsure
<222> LOCATION: (130)
<220> FEATURE:
<221> NAME/KEY: unsure
<222> LOCATION: (132)
<220> FEATURE:
<221> NAME/KEY: unsure
<222> LOCATION: (132)
<220> FEATURE:
<221> NAME/KEY: unsure
<222> LOCATION: (137)
<220> FEATURE:
<221> NAME/KEY: unsure
<222> LOCATION: (139)

```
<220> FEATURE:
<221> NAME/KEY: unsure
<222> LOCATION: (141)
<220> FEATURE:
<221> NAME/KEY: unsure
<222> LOCATION: (145)..(146)
<220> FEATURE:
<221> NAME/KEY: unsure
<222> LOCATION: (148)
<220> FEATURE:
<221> NAME/KEY: unsure
<222> LOCATION: (150)..(151)
<220> FEATURE:
<221> NAME/KEY: unsure
<222> LOCATION: (160)..(162)
<220> FEATURE:
<221> NAME/KEY: unsure
<222> LOCATION: (168)
<220> FEATURE:
<221> NAME/KEY: unsure
<222> LOCATION: (188)

<400> SEQUENCE: 5
ttatggatgg tgaagggaat ggtatagaat tggagagatt atcttactga caactgtag      60 tcccagcttt ctctggaagt ggtggtattt gagcagggtg tgcacaaagg aattttaatn    120
ncccnaaatn gnttttnanc ntttnnanan nattaaaacn nnggtttngg ggggaattgg    180 agggggngntc t                                                        191

<210> SEQ ID NO 6
<211> LENGTH: 647
<212> TYPE: DNA
<213> ORGANISM: Homo sapiens

<400> SEQUENCE: 6
atattatgga tggtgaaggg aatggtatag aattggagag attatcttac tgaacacctg     60
tagtcccagc tttctctgga agtggtggta tttgagcagg atgtgcacaa ggcaattgaa    120
atgcccataa ttagtttctc agctttgaat acactataaa ctcagtggct gaaggaggaa    180
attttagaag gaagctacta aaagatctaa tttgaaaaac tacaaaagca ttaactaaaa    240
aagtttattt tccttttgtc tgggcagtag tgaaaataac tactcacaac attcactatg    300
tttgcaagga attaacacaa ataaaagatg ccttttttact taaacaccaa gacagaaaac    360
ttgcccaata ctgagaagca acttgcatta gagagggaac tgttaaatgt tttcaaccca    420
gttcatctgg tggatgtttt tgcaggttac tctgagaatt ttgcttatga aaaatcatta    480 ttttttagtgt agttcacaat aatgtattga acatacttct aatcaaaggt gctatgtcct    540
tgtgtatggt actaaatgtg tcctgtgtac ttttgcacaa ctgagaatcc tgcagcttgg    600
tttaatgagt gtgttcatga aataaataat ggaggaattg tcaaaaa                  647

<210> SEQ ID NO 7
<211> LENGTH: 320
<212> TYPE: PRT
<213> ORGANISM: Homo sapiens

<400> SEQUENCE: 7

Met Ser Ser Cys Asn Phe Thr His Ala Thr Phe Val Leu Ile Gly Ile
1               5                   10                  15

Pro Gly Leu Glu Lys Ala His Phe Trp Val Gly Phe Pro Leu Leu Ser
            20                  25                  30

Met Tyr Val Val Ala Met Phe Gly Asn Cys Ile Val Val Phe Ile Val
        35                  40                  45
```

```
Arg Thr Glu Arg Ser Leu His Ala Pro Met Tyr Leu Phe Leu Cys Met
    50              55                  60

Leu Ala Ala Ile Asp Leu Ala Leu Ser Thr Ser Thr Met Pro Lys Ile
65              70                  75                  80

Leu Ala Leu Phe Trp Phe Asp Ser Arg Glu Ile Ser Phe Glu Ala Cys
                85                  90                  95

Leu Thr Gln Met Phe Phe Ile His Ala Leu Ser Ala Ile Glu Ser Thr
                100                 105                 110

Ile Leu Leu Ala Met Ala Phe Asp Arg Tyr Val Ala Ile Cys His Pro
            115                 120                 125

Leu Arg His Ala Ala Val Leu Asn Asn Thr Val Thr Ala Gln Ile Gly
    130                 135                 140

Ile Val Ala Val Val Arg Gly Ser Leu Phe Phe Pro Leu Pro Leu
145                 150                 155                 160

Leu Ile Lys Arg Leu Ala Phe Cys His Ser Asn Val Leu Ser His Ser
                165                 170                 175

Tyr Cys Val His Gln Asp Val Met Lys Leu Ala Tyr Ala Asp Thr Leu
                180                 185                 190

Pro Asn Val Val Tyr Gly Leu Thr Ala Ile Leu Leu Val Met Gly Val
                195                 200                 205

Asp Val Met Phe Ile Ser Leu Ser Tyr Phe Leu Ile Ile Arg Thr Val
210                 215                 220

Leu Gln Leu Pro Ser Lys Ser Glu Arg Ala Lys Ala Phe Gly Thr Cys
225                 230                 235                 240

Val Ser His Ile Gly Val Val Leu Ala Phe Tyr Val Pro Leu Ile Gly
                245                 250                 255

Leu Ser Val Val His Arg Phe Gly Asn Ser Leu His Pro Ile Val Arg
                260                 265                 270

Val Val Met Gly Asp Ile Tyr Leu Leu Pro Pro Val Ile Asn Pro
            275                 280                 285

Ile Ile Tyr Gly Ala Lys Thr Lys Gln Ile Arg Thr Arg Val Leu Ala
            290                 295                 300

Met Phe Lys Ile Ser Cys Asp Lys Asp Leu Gln Ala Val Gly Gly Lys
305                 310                 315                 320

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 8
gggcttgtca cagtctctac tgtt                                            24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 9
gccagaacat tgtgagcaca c                                               21

<210> SEQ ID NO 10
<211> LENGTH: 20
<212> TYPE: DNA
```

-continued

```
<213> ORGANISM: Artificial Sequence
<220> FEATURE:
<223> OTHER INFORMATION: Description of Artificial Sequence: Synthetic

<400> SEQUENCE: 10
cgcccatttc tcagatcaag                                              20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 11
cgcccagtag atgtttcaaa g                                            21

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 12
aagggaatgg tatagaattg gagag                                        25

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 13
cctgctcaaa taccaccact tc                                           22
```

METHOD OF DIAGNOSING, MONITORING, STAGING, IMAGING AND TREATING PROSTATE CANCER

This application is a divisional of U.S. patent application Ser. No. 09/730,018 filed Dec. 4, 2000 now abandoned which claims the benefit of priority from U.S. Provisional Application Ser. No. 60/169,083, filed Dec. 6, 1999, each of which are herein incorporated by reference in their entirety.

FIELD OF THE INVENTION

This invention relates, in part, to newly developed assays for detecting, diagnosing, monitoring, staging, prognosticating, imaging and treating cancers, particularly prostate cancer.

BACKGROUND OF THE INVENTION

Cancer of the prostate is the most prevalent malignancy in adult males, excluding skin cancer, and is an increasingly prevalent health problem in the United States. In 1996, it was estimated that 41,400 deaths would result from this disease in the United States alone, indicating that prostate cancer is second only to lung cancer as the most common cause of death in the same population. If diagnosed and treated early, when the cancer is still confined to the prostate, the chances of cure is significantly higher.

Treatment decisions for an individual are linked to the stage of prostate cancer present in that individual. A common classification of the spread of prostate cancer was developed by the American Urological Association (AUA). The AUA system divides prostate tumors into four stages, A to D. Stage A, microscopic cancer within prostate, is further subdivided into stages A1 and A2. Sub-stage A1 is a well-differentiated cancer confined to one site within the prostate. Treatment is generally observation, radical prostatectomy, or radiation. Sub-stage A2 is a moderately to poorly differentiated cancer at multiple sites within the prostate. Treatment is radical prostatectomy or radiation. Stage B, palpable lump within the prostate, is also further subdivided into sub-stages B1 and B2. In sub-stage B1, the cancer forms a small nodule in one lobe of the prostate. In sub-stage B2, the cancer forms large or multiple nodules, or occurs in both lobes of the prostate. Treatment for sub-stages B1 and B2 is either radical prostatectomy or radiation. Stage C is a large cancer mass involving most or all of the prostate and is also further subdivided into two sub-stages. In sub-stage C1, the cancer forms a continuous mass that may have extended beyond the prostate. In sub-stage C2, the cancer forms a continuous mass that invades the surrounding tissue. Treatment for both these sub-stages is radiation with or without drugs to address the cancer. The fourth stage, Stage D is metastatic cancer and is also subdivided into two sub-stages. In sub-stage D1, the cancer appears in the lymph nodes of the pelvis. In sub-stage D2, the cancer involves tissues beyond lymph nodes. Treatment for both of these sub-stages is systemic drugs to address the cancer as well as pain.

However, current prostate cancer staging methods are limited. As many as 50% of prostate cancers initially staged as A2, B, or C are actually stage D, metastatic. Discovery of metastasis is significant because patients with metastatic cancers have a poorer prognosis and require significantly different therapy than those with localized cancers. The five year survival rates for patients with localized and metastatic prostate cancers are 93% and 29%, respectively.

Accordingly, there is a great need for more sensitive and accurate methods for the staging of a cancer in a human to determine whether or not such cancer has metastasized and for monitoring the progress of a cancer in a human which has not metastasized for the onset of metastasis.

Three genes have now been identified as diagnostic arkers for prostate cancer. These diagnostic markers are referred to herein generally as cancer specific genes or CSGs and more specifically as Pro119, Pro121 and Pro124. The nucleotide sequence of Pro119 shares 91% homology with a rat G-protein coupled receptor (Raming et al. Receptor Channels 1998 6(2):141-51). ESTs for these CSGs are set forth as SEQ ID NO: 1, 3 and 5 while the full length contigs for these CSGs are set forth in SEQ ID NO: 2, 4 and 6, respectively. An exemplary protein encoded by Pro119 (SEQ ID NO:1 or 2) is depicted herein as SEQ ID NO:7.

In the present invention, methods are provided for detecting, diagnosing, monitoring, staging, prognosticating, imaging and treating prostate cancer via the cancer specific genes referred to herein as CSGs. For purposes of the present invention, CSG refers, among other things, to native protein expressed by the gene comprising a polynucleotide sequence of SEQ ID NO:1, 2, 3, 4, 5 or 6. An exemplary protein encoded by Pro119 (SEQ ID NO:1 or 2) is depicted herein as SEQ ID NO:7. By "CSG" it is also meant herein polynucleotides which, due to degeneracy in genetic coding, comprise variations in nucleotide sequence as compared to SEQ ID NO: 1-6, but which still encode the same protein. In the alternative, what is meant by CSG as used herein, means the native mRNA encoded by the gene comprising the polynucleotide sequence of SEQ ID NO:1, 2, 3, 4, 5 or 6, levels of the gene comprising the polynucleotide sequence of SEQ ID NO:1, 2, 3, 4, 5 or 6, or levels of a polynucleotide which is capable of hybridizing under stringent conditions to the antisense sequence of SEQ ID NO:1, 2, 3, 4, 5 or 6.

Other objects, features, advantages and aspects of the present invention will become apparent to those of skill in the art from the following description. It should be understood, however, that the following description and the specific examples, while indicating preferred embodiments of the invention are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide CSGs comprising a polynucleotide of SEQ ID NO:1, 2, 3, 4, 5, or 6 or a variant thereof, a protein expressed by a polynucleotide of SEQ ID NO:1, 2, 3, 4, 5, or 6 or variant thereof which expresses the protein; or a polynucleotide which is capable of hybridizing under stringent conditions to the antisense sequence of SEQ ID NO: 1, 2, 3, 4, 5, or 6.

Further provided is a method for diagnosing the presence of prostate cancer by analyzing for changes in levels of CSG in cells, tissues or bodily fluids compared with levels of CSG in preferably the same cells, tissues, or bodily fluid type of a normal human control, wherein a change in levels of CSG in the patient versus the normal human control is associated with prostate cancer.

Further provided is a method of diagnosing metastatic prostate cancer in a patient having prostate cancer which is not known to have metastasized by identifying a human patient suspected of having prostate cancer that has metastasized; analyzing a sample of cells, tissues, or bodily fluid from such patient for CSG; comparing the CSG levels in such cells, tissues, or bodily fluid with levels of CSG in preferably the same cells, tissues, or bodily fluid type of a normal human control, wherein an increase in CSG levels in the patient versus the normal human control is associated with prostate cancer which has metastasized.

Also provided by the invention is a method of staging prostate cancer in a human which has such cancer by identifying a human patient having such cancer; analyzing a sample of cells, tissues, or bodily fluid from such patient for CSG; comparing CSG levels in such cells, tissues, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided is a method of monitoring prostate cancer in a human having such cancer for the onset of metastasis. The method comprises identifying a human patient having such cancer that is not known to have metastasized; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which has metastasized.

Further provided is a method of monitoring the change in stage of prostate cancer in a human having such cancer by looking at levels of CSG in a human having such cancer. The method comprises identifying a human patient having such cancer; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided are methods of designing new therapeutic agents targeted to CSGs for use in imaging and treating cancer. For example, in one embodiment, therapeutic agents such as antibodies targeted against a CSG or fragments of such antibodies can be used to treat, detect or image localization of a CSG in a patient for the purpose of detecting or diagnosing a disease or condition. In this embodiment, an increase in the amount of labeled antibody detected as compared to normal tissue would be indicative of tumor metastases or growth. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. Therapeutics agents such as small molecule and antibodies or fragments thereof which decrease the concentration and/or activity of a CSG can also be used in the treatment of diseases characterized by overexpression of CSG. In these applications, the antibody can be used without or with derivatization to a cytotoxic agent such as a radioisotope, enzyme, toxin, drug or a prodrug.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

The present invention relates to diagnostic assays and methods, both quantitative and qualitative for detecting, diagnosing, monitoring, staging and prognosticating cancers by comparing levels of CSG in a human patient with those of CSG in a normal human control. For purposes of the present invention, what is meant by CSG levels is, among other things, native protein expressed by the gene comprising a polynucleotide sequence of SEQ ID NO:1, 2, 3, 4, 5 or 6. An exemplary protein encoded by the CSG Pro119 (SEQ ID NO:1 or 2) is depicted herein as SEQ ID NO:7. By "CSG" it is also meant herein polynucleotides which, due to degeneracy in genetic coding, comprise variations in nucleotide sequence as compared to SEQ ID NO: 1-6, but which still encode the same protein. The native protein being detected, may be whole, a breakdown product, a complex of molecules or chemically modified. In the alternative, what is meant by CSG as used herein, means the native mRNA encoded by the gene comprising the polynucleotide sequence of SEQ ID NO:1, 2, 3, 4, 5 or 6, levels of the gene comprising the polynucleotide sequence of SEQ ID NO:1, 2, 3, 4, 5 or 6, or levels of a polynucleotide which is capable of hybridizing under stringent conditions to the antisense sequence of SEQ ID NO:1, 2, 3, 4, 5 or 6. Such levels are preferably determined in at least one of, cells, tissues and/or bodily fluids, including determination of normal and abnormal levels. Thus, for instance, a diagnostic assay in accordance with the invention for diagnosing overexpression of CSG protein compared to normal control bodily fluids, cells, or tissue samples may be used to diagnose the presence of prostate cancer.

All the methods of the present invention may optionally include determining the levels of other cancer markers as well as CSG. Other cancer markers, in addition to CSG, useful in the present invention will depend on the cancer being tested and are known to those of skill in the art.

Diagnostic Assays

The present invention provides methods for diagnosing the presence of prostate cancer by analyzing for changes in levels of CSG in cells, tissues or bodily fluids compared with levels of CSG in cells, tissues or bodily fluids of preferably the same type from a normal human control, wherein an increase in levels of CSG in the patient versus the normal human control is associated with the presence of prostate cancer.

Without limiting the instant invention, typically, for a quantitative diagnostic assay a positive result indicating the patient being tested has cancer is one in which cells, tissues or bodily fluid levels of the cancer marker, such as CSG, are at least two times higher, and most preferably are at least five times higher, than in preferably the same cells, tissues or bodily fluid of a normal human control.

The present invention also provides a method of diagnosing metastatic prostate cancer in a patient having prostate cancer which has not yet metastasized for the onset of metastasis. In the method of the present invention, a human cancer patient suspected of having prostate cancer which may have metastasized (but which was not previously known to have metastasized) is identified. This is accomplished by a variety of means known to those of skill in the art.

In the present invention, determining the presence of CSG levels in cells, tissues or bodily fluid, is particularly useful for discriminating between prostate cancer which has not metastasized and prostate cancer which has metastasized. Existing techniques have difficulty discriminating between prostate cancer which has metastasized and prostate cancer which has not metastasized and proper treatment selection is often dependent upon such knowledge.

In the present invention, the cancer marker levels measured in such cells, tissues or bodily fluid is CSG, and are compared with levels of CSG in preferably the same cells, tissue or bodily fluid type of a normal human control. That is, if the cancer marker being observed is just CSG in serum, this level is preferably compared with the level of CSG in serum of a normal human control. An increase in the CSG in the patient versus the normal human control is associated with prostate cancer which has metastasized.

Without limiting the instant invention, typically, for a quantitative diagnostic assay a positive result indicating the cancer in the patient being tested or monitored has metastasized is one in which cells, tissues or bodily fluid levels of the cancer marker, such as CSG, are at least two times higher, and most preferably are at least five times higher, than in preferably the same cells, tissues or bodily fluid of a normal patient.

Normal human control as used herein includes a human patient without cancer and/or non cancerous samples from the patient; in the methods for diagnosing or monitoring for metastasis, normal human control may preferably also include samples from a human patient that is determined by reliable methods to have prostate cancer which has not metastasized.

Staging

The invention also provides a method of staging prostate cancer in a human patient. The method comprises identifying a human patient having such cancer and analyzing cells, tissues or bodily fluid from such human patient for CSG. The CSG levels determined in the patient are then compared with levels of CSG in preferably the same cells, tissues or bodily fluid type of a normal human control, wherein an increase in the CSG levels in the human patient versus the normal human control is associated with a cancer which is progressing and a decrease in the levels of CSG (but still increased over true normal levels) is associated with a cancer which is regressing or in remission.

Monitoring

Further provided is a method of monitoring prostate cancer in a human patient having such cancer for the onset of metastasis. The method comprises identifying a human patient having such cancer that is not known to have metastasized; periodically analyzing cells, tissues or bodily fluid from such human patient for CSG; and comparing the CSG levels determined in the human patient with levels of CSG in preferably the same cells, tissues or bodily fluid type of a normal human control, wherein an increase in CSG levels in the human patient versus the normal human control is associated with a cancer which has metastasized. In this method, normal human control samples may also include prior patient samples.

Further provided by this invention is a method of monitoring the change in stage of prostate cancer in a human patient having such cancer. The method comprises identifying a human patient having such cancer; periodically analyzing cells, tissues or bodily fluid from such human patient for CSG; and comparing the CSG levels determined in the human patient with levels of CSG in preferably the same cells, tissues or bodily fluid type of a normal human control, wherein an increase in CSG levels in the human patient versus the normal human control is associated with a cancer which is progressing in stage and a decrease in the levels of CSG is associated with a cancer which is regressing in stage or in remission. In this method, normal human control samples may also include prior patient samples.

Monitoring a patient for onset of metastasis is periodic and preferably done on a quarterly basis. However, this may be more or less frequent depending on the cancer, the particular patient, and the stage of the cancer.

Prognostic Testing and Clinical Trial Monitoring

The methods described herein can further be utilized as prognostic assays to identify subjects having or at risk of developing a disease or disorder associated with increased levels of CSG. The present invention provides a method in which a test sample is obtained from a human patient and CSG is detected. The presence of higher CSG levels as compared to normal human controls is diagnostic for the human patient being at risk for developing cancer, particularly prostate cancer.

The effectiveness of therapeutic agents to decrease expression or activity of the CSGs of the invention can also be monitored by analyzing levels of expression of the CSGs in a human patient in clinical trials or in in vitro screening assays such as in human cells. In this way, the gene expression pattern can serve as a marker, indicative of the physiological response of the human patient, or cells as the case may be, to the agent being tested.

Detection of Genetic Lesions or Mutations

The methods of the present invention can also be used to detect genetic lesions or mutations in CSG, thereby determining if a human with the genetic lesion is at risk for prostate cancer or has prostate cancer. Genetic lesions can be detected, for example, by ascertaining the existence of a deletion and/or addition and/or substitution of one or more nucleotides from the CSGs of this invention, a chromosomal rearrangement of CSG, aberrant modification of CSG (such as of the methylation pattern of the genomic DNA), the presence of a non-wild type splicing pattern of a mRNA transcript of CSG, allelic loss of CSG, and/or inappropriate post-translational modification of CSG protein. Methods to detect such lesions in the CSG of this invention are known to those of skill in the art.

Assay Techniques

Assay techniques that can be used to determine levels of gene expression, such as CSG of the present invention, in a sample derived from a human are well-known to those of skill in the art. Such assay methods include radioimmunoassays, reverse transcriptase PCR (RT-PCR) assays, immunohistochemistry assays, in situ hybridization assays, competitive-binding assays, Western Blot analyses, ELISA assays and proteomic approaches, two-dimensional gel electrophoresis (2D electrophoresis) and non-gel based approaches such as mass spectrometry or protein interaction profiling.

Among these, ELISAs are frequently preferred to diagnose a gene's expressed protein in biological fluids.

An ELISA assay initially comprises preparing an antibody, if not readily available from a commercial source, specific to CSG, preferably a monoclonal antibody. In addition a reporter antibody generally is prepared which binds specifically to CSG. The reporter antibody is attached to a detectable reagent such as a radioactive, fluorescent or enzymatic reagent, for example horseradish peroxidase enzyme or alkaline phosphatase.

To carry out the ELISA, antibody specific to CSG is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time CSG binds to the specific antibody attached to the polystyrene dish. Unbound sample is washed out with buffer. A reporter antibody specifically directed to CSG and linked to a detectable reagent such as horseradish peroxidase is placed in the dish resulting in binding of the reporter antibody to any monoclonal antibody bound to CSG. Unattached reporter antibody is then washed out. Reagents for peroxidase activity, including a calorimetric substrate are then added to the dish. Immobilized peroxidase, linked to CSG antibodies, produces a colored reaction product. The amount of color developed in a given time period is proportional to the amount of CSG protein present in the sample. Quantitative results typically are obtained by reference to a standard curve.

A competition assay can also be employed wherein antibodies specific to CSG are attached to a solid support and labeled CSG and a sample derived from the patient or human control are passed over the solid support. The amount of label detected which is attached to the solid support can be correlated to a quantity of CSG in the sample.

Using all or a portion of a nucleic acid sequence of a CSG of the present invention as a hybridization probe, nucleic acid methods can also be used to detect CSG mRNA as a marker for cancer, and in particular prostate cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e., gridding) can be used to both detect the expression of and quantitate the level of expression of that gene. In this approach, a cDNA encoding a CSG gene is fixed to a substrate. The substrate may be of any suitable type including but not limited to glass, nitrocellulose, nylon or plastic. At least a portion of the DNA encoding the CSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety cells, bodily fluids and/or tissue extracts (homogenates or solubilized tissue) obtained from the patient including tissue biopsy and autopsy material. Bodily fluids useful in the present invention include blood, urine, saliva, or any other bodily secretion or derivative thereof. Blood can include whole blood, plasma, serum, or any derivative of blood.

In Vivo Targeting of CSGs/Prostate Cancer Therapy

Identification of CSGs is also useful in the rational design of new therapeutics for imaging and treating cancers, and in particular prostate cancer. For example, in one embodiment, antibodies which specifically bind to CSGs can be raised and used in vivo in patients suspected of suffering from cancer. Antibodies which specifically bind a CSG can be injected into a patient suspected of having cancer for diagnostic and/or therapeutic purposes. The preparation and use of antibodies for in vivo diagnosis is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247-254). In particular, these antibody-chelators have been used in detecting tumors in patients suspected of having recurrent colorectal cancer (Griffin et al. J. Clin. Onc. 1991 9:631-640). Antibodies with paramagnetic ions as labels for use in magnetic resonance imaging have also been described (Lauffer, R. B. Magnetic Resonance in Medicine 1991 22:339-342). Antibodies directed against CSGs can be used in a similar manner. Labeled antibodies which specifically bind a CSG can be injected into patients suspected of having prostate cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Localization of the label permits determination of the spread of the cancer. The amount of label within an organ or tissue also allows determination of the presence or absence of cancer in that organ or tissue.

For patients diagnosed with cancer, and in particular prostate cancer, injection of an antibody which specifically binds a CSG can also have a therapeutic benefit. The antibody may exert its therapeutic effect alone. Alternatively, the antibody can be conjugated to a cytotoxic agent such as a drug, toxin or radionuclide to enhance its therapeutic effect. Drug monoclonal antibodies have been described in the art for example by Garnett and Baldwin, Cancer Research 1986 46:2407-2412. The use of toxins conjugated to monoclonal antibodies for the therapy of various cancers has also been described by Pastan et al. Cell 1986 47:641-648. Yttrium-90 labeled monoclonal antibodies have been described for maximization of dose delivered to the tumor while limiting toxicity to normal tissues (Goodwin and Meares Cancer Supplement 1997 80:2675-2680). Other cytotoxic radionuclides including, but not limited to Copper-67, Iodine-131 and Rhenium-186 can also be used for labeling of antibodies against CSG.

Antibodies which can be used in these in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

Screening Assays

The present invention also provides methods for identifying modulators which bind to CSG protein or have a modulatory effect on the expression or activity of CSG protein. Modulators which decrease the expression or activity of CSG protein are believed to be useful in treating prostate cancer. Such screening assays are known to those of skill in the art and include, without limitation, cell-based assays and cell free assays.

Small molecules predicted via computer imaging to specifically bind to regions of CSG can also be designed, synthesized and tested for use in the imaging and treatment of prostate cancer. Further, libraries of molecules can be screened for potential anticancer agents by assessing the ability of the molecule to bind to the CSGs identified herein. Molecules identified in the library as being capable of binding to CSG are key candidates for further evaluation for use in the treatment of prostate cancer. In a preferred embodiment, these molecules will downregulate expression and/or activity of CSG in cells.

Adoptive Immunotherapy and Vaccines

Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category and investigators at the National Cancer Institute (NCI) have used autologous reinfusion of peripheral blood lymphocytes or tumor-infiltrating lymphocytes (TIL), T cell cultures from biopsies of subcutaneous lymph nodules, to treat several human cancers (Rosenberg, S. A., U.S. Pat. No. 4,690,914, issued Sep. 1, 1987; Rosenberg, S. A., et al., 1988, N. England J. Med. 319:1676-1680).

The present invention relates to compositions and methods of adoptive immunotherapy for the prevention and/or treatment of primary and metastatic prostate cancer in humans using macrophages sensitized to the antigenic CSG molecules, with or without non-covalent complexes of heat shock protein (hsp). Antigenicity or immunogenicity of the CSG is readily confirmed by the ability of the CSG protein or a fragment thereof to raise antibodies or educate naive effector cells, which in turn lyse target cells expressing the antigen (or epitope). Cancer cells are, by definition, abnormal and contain proteins which should be recognized by the immune system as foreign since they are not present in normal tissues. However, the immune system often seems to ignore this abnormality and fails to attack tumors. The foreign CSG proteins that are produced by the cancer cells can be used to reveal their presence. The CSG is broken into short fragments, called tumor antigens, which are displayed on the surface of the cell. These tumor antigens are held or presented on the cell surface by molecules called MHC, of which there are two types: class I and II. Tumor antigens in association with MHC class I molecules are recognized by cytotoxic T cells while antigen-MHC class II complexes are recognized by a second subset of T cells called helper cells. These cells secrete cytokines which slow or stop tumor growth and help another type of white blood cell, B cells, to make antibodies against the tumor cells.

In adoptive immunotherapy, T cells or other antigen presenting cells (APCs) are stimulated outside the body (ex vivo), using the tumor specific CSG antigen. The stimulated cells are then reinfused into the patient where they attack the cancerous cells. Research has shown that using both cytotoxic and helper T cells is far more effective than using either subset alone. Additionally, the CSG antigen may be complexed with heat shock proteins to stimulate the APCs as described in U.S. Pat. No. 5,985,270.

The APCs can be selected from among those antigen presenting cells known in the art including, but not limited to, macrophages, dendritic cells, B lymphocytes, and a combination thereof, and are preferably macrophages. In a preferred use, wherein cells are autologous to the individual, autologous immune cells such as lymphocytes, macrophages or other APCs are used to circumvent the issue of whom to select as the donor of the immune cells for adoptive transfer. Another problem circumvented by use of autologous immune cells is graft versus host disease which can be fatal if unsuccessfully treated.

In adoptive immunotherapy with gene therapy, DNA of the CSG can be introduced into effector cells similarly as in conventional gene therapy. This can enhance the cytotoxicity of the effector cells to tumor cells as they have been manipulated to produce the antigenic protein resulting in improvement of the adoptive immunotherapy.

CSG antigens of this invention are also useful as components of prostate cancer vaccines. The vaccine comprises an immunogenically stimulatory amount of a CSG antigen. Immunogenically stimulatory amount refers to that amount of antigen that is able to invoke the desired immune response in the recipient for the amelioration, or treatment of prostate cancer. Effective amounts may be determined empirically by standard procedures well known to those skilled in the art.

The CSG antigen may be provided in any one of a number of vaccine formulations which are designed to induce the desired type of immune response, e.g., antibody and/or cell mediated. Such formulations are known in the art and include, but are not limited to, formulations such as those described in U.S. Pat. No. 5,585,103. Vaccine formulations of the present invention used to stimulate immune responses can also include pharmaceutically acceptable adjuvants.

EXAMPLES

The present invention is further described by the following example. The example is provided solely to illustrate the invention by reference to specific embodiments. This exemplification, while illustrating certain aspects of the invention, do not portray the limitations or circumscribe the scope of the disclosed invention.

All examples outlined here were carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Relative Quantitation of Gene Expression

Real-Time quantitative PCR with fluorescent TAQMAN probes is a quantitation detection system utilizing the 5'-3' nuclease activity of Taq DNA polymerase. The method uses an internal fluorescent oligonucleotide probe (TAQMAN) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH), ATPase, or 18S ribosomal RNA (rRNA) is used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene were evaluated for every sample in normal and cancer tissues. Total RNA was extracted from normal tissues, cancer tissues, and from cancers and the corresponding matched adjacent tissues. Subsequently, first strand cDNA was prepared with reverse transcriptase and the polymerase chain reaction was done using primers and Taqman probes specific to each target gene. The results were analyzed using the ABI PRISM 7700 Sequence Detector. The absolute numbers are relative levels of expression of the target gene in a particular tissue compared to the calibrator tissue.

Expression of Clone ID 824430 (Pro119):

For the CSG Pro119, real-time quantitative PCR was performed using the following primers:

Forward Primer:
5'-GGGCTTGTCACAGTCTCTACTGTT-3' (SEQ ID NO:8)

Reverse Primer:
5'-GCCAGAACATTGTGAGCACAC-3' (SEQ ID NO:9)

The absolute numbers depicted in Table 1 are relative levels of expression of the CSG referred to as Pro119 in 12 normal different tissues. All the values are compared to normal prostate (calibrator). These RNA samples are commercially available pools, originated by pooling samples of a particular tissue from different individuals.

TABLE 1

Relative Levels of CSG Pro119 Expression in Pooled Samples

| Tissue | NORMAL |
|---|---|
| Brain | 0.002 |
| Heart | 0.001 |
| Kidney | 0.001 |
| Liver | 0.003 |
| Lung | 0.006 |
| Mammary | 0.003 |
| Muscle | 0.003 |
| Prostate | 1 |
| Small Intestine | 0.006 |
| Testis | 0.009 |
| Thymus | 0.003 |
| Uterus | 0.02 |

The relative levels of expression in Table 1 show that Pro119 mRNA expression is higher in prostate (1.0) compared with all other normal tissues analyzed. All other tissues analyzed show a relative Pro119 mRNA expression of less than one.

The absolute numbers in Table 1 were obtained analyzing pools of samples of a particular tissue from different individuals. They cannot be compared to the absolute numbers originated from RNA obtained from tissue samples of a single individual in Table 2.

The absolute numbers depicted in Table 2 are relative levels of expression of Pro119 in 49 pairs of matched and 15 unmatched samples. All the values are compared to normal prostate (calibrator). A matching pair is formed by obtaining mRNA from the cancer sample for a particular tissue and mRNA from the normal adjacent sample for that same tissue from the same individual.

TABLE 2

Relative Levels of CSG Pro119 Expression in Individual Samples

| Sample ID | Tissue | Cancer | Matching Normal Adjacent |
|---|---|---|---|
| Pro12B | Prostate 1 | 0.13 | 0.16 |
| ProC234 | Prostate 2 | 1.73 | |
| Pro78XB | Prostate 3 | 15.9 | 2.9 |
| Pro109XB | Prostate 4 | 0.13 | 0.21 |
| Pro84XB | Prostate 5 | 25.79 | 0.49 |
| Pro101XB | Prostate 6 | 20.33 | 9.35 |
| Pro91X | Prostate 7 | 19.26 | 0.85 |
| Pro13XB | Prostate 8 | 0.07 | 0.16 |
| ProC215 | Prostate 9 | 4.52 | |
| Pro125XB | Prostate 10 | 0.09 | 0.05 |
| Pro23B | Prostate 11 | 0.86 | 1.05 |
| Pro90XB | Prostate 12 | 0.01 | 0.23 |
| ProC280 | Prostate 13 | 0.28 | |
| Pro20XB | Prostate 14 | 2.68 | 0 |
| Pro34B | Prostate 15 | 2.96 | 1.84 |
| Pro110 | Prostate 16 | 0.19 | 0.5 |
| Pro65XB | Prostate 17 | 16.02 | 0.01 |
| Pro69XB | Prostate 18 | 2.26 | 1.02 |
| Pro326 | Prostate 19 | 0.81 | 0.72 |
| Pro10R | Prostate 20 (Prostatitis) | 1.68 | |
| Pro20R | Prostate 21 (Prostatitis) | 0.71 | |
| ProC258 | Prostate 22 (BPH) | 0.03 | |
| Pro263C | Prostate 23 (BPH) | 4.37 | |

TABLE 2-continued

Relative Levels of CSG Pro119 Expression in Individual Samples

| Sample ID | Tissue | Cancer | Matching Normal Adjacent |
|---|---|---|---|
| Pro267A | Prostate 24 (BPH) | 0.02 | |
| Pro271A | Prostate 25 (BPH) | 0.49 | |
| Pro460Z | Prostate 26 (BPH) | 0.4 | |
| ProC032 | Prostate 27 (BPH) | 0.97 | |
| Bld32XK | Bladder 1 | 0 | 0.01 |
| Bld46XK | Bladder 2 | 0.01 | 0.01 |
| Bld66X | Bladder 3 | 0.02 | 0 |
| Kid106XD | Kidney 1 | 0.01 | 0 |
| Kid107XD | Kidney 2 | 0 | 0 |
| Kid109XD | Kidney 3 | 0.02 | 0 |
| Tst239X/240X | Testis 1 | 0.004 | 0.004 |
| Tst S9820647A/B | Testis 2 | 0.03 | 0.01 |
| Tst S9820663A/B | Testis 3 | 0 | 0 |
| Skn248S | Skin 1 | 0.03 | 0 |
| Skn287S | Skin 2 | 0 | 0 |
| SmI9807A212A/213A | Small Intestine 1 | 0.01 | 0.004 |
| SmI9802H008/H009 | Small Intestine 2 | 0.003 | 0.001 |
| ClnAC19 | Colon 1 | 0.02 | 0.62 |
| ClnAS12 | Colon 2 | 0.01 | 0.32 |
| ClnAS43 | Colon 3 | 0.02 | 0.15 |
| Sto115S | Stomach 1 | 0 | 0.02 |
| Sto15S | Stomach 2 | 0.01 | 0 |
| Sto17S | Stomach 3 | 0.01 | 0.01 |
| Lng476Q/477Q | Lung 1 | 0 | 0 |
| Lng60XL | Lung 2 | 0 | 0 |
| Lng75XC | Lung 3 | 0 | 0 |
| Pan921O/922O | Pancreas 1 | 0.01 | 0.02 |
| Pan9408C044R/45R | Pancreas 2 | 0 | 0 |
| Pan82XP | Pancreas 3 | 0.01 | 0 |
| Utr1359O/1358O | Uterus 1 | 0.05 | 0 |
| Utr1417O/1418O | Uterus 2 | 0 | 0.02 |
| Utr233U96/234U96 | Uterus 3 | 0.03 | 0.01 |
| Utr850U/851U | Uterus 4 | 0.01 | 0.03 |
| End10479B/10479D | Endometrium 1 | 0.04 | 0.13 |
| End9705A125A/126A | Endometrium 2 | 0 | 0.02 |
| Mam14153a1c/a2f | Mammary Gland 1 | 0 | 0 |
| Mam00014D05/N05 | Mammary Gland 2 | 0.1 | 0 |
| Mam162X | Mammary Gland 3 | 0 | 0 |
| Mam19DN | Mammary Gland 4 | 0 | 0 |
| Ovr1005O | Ovary 1 | 0.001 | |
| Ovr1028O | Ovary 2 | 0.03 | |
| Ovr1037O/1038O | Ovary 3 | 0.02 | 0.004 |
| Ovr9702C018G | Ovary 4 | | 0.03 |
| Ovr206I | Ovary 5 | | 0.02 |

0 = Negative

In the analysis of matching samples, the higher levels of expression were in prostate, showing a high degree of tissue specificity for prostate tissue. Eleven of 16 prostate matching samples showed upregulation in Pro119 mRNA expression. Of all the samples different than prostate analyzed, no other cancer or normal tissue sample showed expression levels comparable to the mRNA expression in prostate. These results confirm a high degree of tissue specificity as obtained with the panel of normal pooled samples (Table 1).

Furthermore, the level of mRNA expression in cancer samples and the isogenic normal adjacent tissue from the same individual were compared. This comparison provides an indication of specificity for the cancer (e.g. higher levels of mRNA expression in the cancer sample compared to the normal adjacent). Table 2 shows overexpression of Pro119 in 11 out of 16 primary prostate cancer tissues compared with their respective normal adjacent. Thus, there was overexpression in the cancer tissue for 68.75% of the prostate matching samples tested.

Altogether, the high degree of tissue specificity, plus the mRNA overexpression in 68.75% of the prostate matching samples tested are indicative of Pro119 being a diagnostic marker for prostate cancer.

Expression of Clone ID788274 (Pro121):

For the CSG Pro121, real-time quantitative PCR was performed using the following primers:

```
Forward Primer
5'-CGCCCATTTCTCAGATCAAG-3'      (SEQ ID NO:10)

Reverse Primer
5'-CGCCCAGTAGATGTTTCAAAG-3'    (SEQ ID NO:11)
```

The absolute numbers depicted in Table 3 are relative levels of expression of the CSG Pro121 in 12 normal different tissues. All the values are compared to normal testis (calibrator). These RNA samples are commercially available pools, originated by pooling samples of a particular tissue from different individuals.

TABLE 3

Relative Levels of CSG Pro121 Expression in Pooled Samples

| Tissue | NORMAL |
|---|---|
| Brain | 0 |
| Heart | 0 |
| Kidney | 0 |
| Liver | 0 |
| Lung | 0 |
| Mammary | 0 |
| Muscle | 0.2 |
| Prostate | 1612.4 |
| Small Intestines | 0.14 |
| Testis | 1 |
| Thymus | 0 |
| Uterus | 1.5 |

The relative levels of expression in Table 3 show that Pro121 mRNA expression is significantly higher (1612.4) in prostate compared with all other normal tissues analyzed. All other tissues analyzed show a relative Pro121 mRNA expression of zero except uterus (1.5), testis (1.0), muscle (0.2) and small intestine (0.14).

The absolute numbers in Table 3 were obtained analyzing pools of samples of a particular tissue from different individuals. They cannot be compared to the absolute numbers originated from RNA obtained from tissue samples of a single individual in Table 4.

The absolute numbers depicted in Table 4 are relative levels of expression of Pro121 in 50 pairs of matched and 16 unmatched samples. All the values are compared to normal testis (calibrator). A matching pair is formed by obtaining mRNA from the cancer sample for a particular tissue and mRNA from the normal adjacent sample for that same tissue from the same individual.

TABLE 4

Relative Levels of CSG Pro121 Expression in Individual Samples

| Sample ID | Tissue | Cancer | Matching Normal Adjacent |
|---|---|---|---|
| Pro12B | Prostate 1 | 15883.4 | 882.21 |
| ProC234 | Prostate 2 | 2511.6 | |
| Pro78XB | Prostate 3 | 2872.6 | 4651 |
| Pro109XB | Prostate 4 | 311.71 | 219.03 |
| Pro84XB | Prostate 5 | 14512.7 | 4907.8 |
| Pro101XB | Prostate 6 | 24876.1 | 14314.9 |
| Pro91X | Prostate 7 | 7553.7 | 1623.6 |
| Pro13XB | Prostate 8 | 84.93 | 31.57 |
| ProC215 | Prostate 9 | 12917.2 | |
| Pro125XB | Prostate 10 | 50.39 | 294.49 |
| Pro23B | Prostate 11 | 8085.9 | 3571.47 |
| Pro90XB | Prostate 12 | 16670.2 | 4597 |
| ProC280 | Prostate 13 | 13219.8 | |
| Pro20XB | Prostate 14 | 2782.6 | 0 |
| Pro34B | Prostate 15 | 14913.87 | 8575.76 |
| Pro110 | Prostate 16 | 4046.55 | 5231.36 |
| Pro65XB | Prostate 17 | 3064.75 | 7879.12 |
| Pro69XB | Prostate 18 | 222.4 | 151.7 |
| Pro326 | Prostate 19 | 14179.84 | 4748.68 |
| Pro10R | Prostate 20 (Prostatitis) | 4025.72 | |
| Pro20R | Prostate 21 (Prostatitis) | 3917.86 | |
| ProC258 | Prostate 22 (BPH) | 1083.11 | |
| Pro263C | Prostate 23 (BPH) | 3436.64 | |
| Pro267A | Prostate 24 (BPH) | 1295.86 | |
| Pro271A | Prostate 25 (BPH) | 614 | |
| Pro460Z | Prostate 26 (BPH) | 2682.9 | |
| ProC032 | Prostate 27 (BPH) | 489.48 | |
| Bld32XK | Bladder 1 | 2.55 | 31.64 |
| Bld46XK | Bladder 2 | 5.58 | 7.52 |
| Bld66X | Bladder 3 | 1823.8 | 0 |
| Kid106XD | Kidney 1 | 0 | 0 |
| Kid107XD | Kidney 2 | 0 | 0 |
| Kid109XD | Kidney 3 | 0 | 0 |
| Tst239X/240X | Testis 1 | 34.27 | 0 |
| TstS9820647A/B | Testis 2 | 0 | 0 |
| TstS9820663 | Testis 3 | 189.7 | 0 |
| Sto115S | Stomach 1 | 0 | 0 |
| Sto15S | Stomach 2 | 37.79 | 0 |
| Sto17S | Stomach 3 | 78.42 | 0 |
| SmI9807A212A/213A | Small Intestine 1 | 0.88 | 0 |
| SmI9802H008/H009 | Small Intestine 2 | 2.04 | 0 |
| ClnAC19 | Colon 1 | 377.3 | 0 |
| ClnAS12 | Colon 2 | 1308.8 | 0 |
| ClnAS43 | Colon 3 | 0 | 0 |
| Lng476Q/477Q | Lung 1 | 0 | 0 |
| Lng60XL | Lung 2 | 0 | 0 |
| Lng75XC | Lung 3 | 0 | 0 |
| Pan921O/922O | Pancreas 1 | 0 | 0 |
| Pan9408C044R/45R | Pancreas 2 | 0 | 0 |
| Pan82XP | Pancreas 3 | 1.03 | 0 |
| Skn248S | Skin 1 | 0 | 0 |
| Skn287S | Skin 2 | 0 | 0 |
| Utr1359O/1358O | Uterus 1 | 0 | 0 |
| Utr1417O/1418O | Uterus 2 | 0 | 0 |
| Utr233U96/234U96 | Uterus 3 | 4.5 | 0 |
| Utr850U/851U | Uterus 4 | 0 | 0 |
| End10479B/10479D | Endometrium 1 | 89.13 | 0 |
| End9705A125A/126A | Endometrium 2 | 0 | 0 |
| Mam14153a1c/a2f | Mammary Gland 1 | 0 | 0 |
| Mam00014D05/N05 | Mammary Gland 2 | 0 | 0 |
| Mam162X | Mammary Gland 3 | 0 | 1.28 |
| Mam14DN | Mammary Gland 4 | 0 | 0 |
| Mam19DN | Mammary Gland 5 | 0 | 0 |
| Ovr1005O | Ovary 1 | 2.68 | |
| Ovr1028O | Ovary 2 | 0 | |
| Ovr1037O/1038O | Ovary 3 | 0 | 0 |
| Ovr9702C018G | Ovary 4 | | 0 |
| Ovr206I | Ovary 5 | | 0 |

In the analysis of matching samples, the higher levels of expression were in prostate, showing a high degree of tissue specificity for prostate tissue. Of all the samples different than prostate analyzed, only 2 cancer samples (the cancer sample bladder 3 with 1823.8 and colon 2 with 1308.8 showed an expression comparable to the mRNA expression in prostate. Other cancer tissues with some expression were: cancer samples colon 1 (377.3), testis 3 (189.7), stomach 3 (78.42), stomach 2 (37.79), testis 1 (34.27), bladder 2 (5.58) and normal adjacent tissue samples bladder 1 (31.64) and bladder 2 (7.52). All remaining tissue samples had relative Pro121 mRNA expression levels of less than 5. These results confirmed a high degree of tissue specificity as obtained with the panel of normal pooled samples (Table 3).

Furthermore, the level of mRNA expression in cancer samples and the isogenic normal adjacent tissue from the same individual were compared. This comparison provides an indication of specificity for the cancer (e.g. higher levels of mRNA expression in the cancer sample compared to the normal adjacent). Table 4 shows overexpression of Pro121 in 12 out of 16 primary prostate cancer tissues compared with their respective normal adjacent. Thus, there was overexpression in the cancer tissue for 75% of the prostate matching samples tested.

Altogether, a high tissue specificity, plus the mRNA overexpression in 75% of the prostate matching samples tested are indicative of Pro121 being a diagnostic marker for prostate cancer.

Expression of Clone ID 832357 (Pro124):

For the CSG Pro124, real-time quantitative PCR was performed using the following primers:

```
Forward Primer
5'-AAGGGAATGGTATAGAATTGGAGAG-3'    (SEQ ID NO:12)

Reverse Primer
5'-CCTGCTCAAATACCACCACTTC-3'       (SEQ ID NO:13)
```

The absolute numbers depicted in Table 5 are relative levels of expression of the CSG Pro124 in 12 normal different tissues. All the values are compared to normal testis (calibrator). These RNA samples are commercially available pools, originated by pooling samples of a particular tissue from different individuals.

TABLE 5

Relative Levels of CSG Pro124 Expression in Pooled Samples

| Tissue | NORMAL |
|---|---|
| Brain | 0.26 |
| Heart | 0 |
| Kidney | 0 |
| Liver | 9.19 |
| Lung | 0 |
| Mammary | 0.05 |
| Muscle | 0 |
| Prostate | 117.38 |
| Small Intestine | 0 |
| Testis | 1 |
| Thymus | 0.4 |
| Uterus | 0.92 |

The relative levels of expression in Table 5 show that Pro124 mRNA expression is very high in normal prostate (117.38) compared with all the other normal tissues analyzed. While some expression was seen in liver (9.19), all other normal tissues had an expression level of 1 or lower.

The absolute numbers in Table 5 were obtained analyzing pools of samples of a particular tissue from different individuals. They cannot be compared to the absolute numbers originated from RNA obtained from tissue samples of a single individual in Table 6.

The absolute numbers depicted in Table 6 are relative levels of expression of Pro124 in 63 pairs of matching and 35 unmatched samples. All the values are compared to normal testis (calibrator). A matching pair is formed by obtaining mRNA from the cancer sample for a particular tissue and mRNA from the normal adjacent sample for that same tissue from the same individual.

TABLE 6

Relative Levels of CSG Pro124 Expression in Individual Samples

| Sample ID | Tissue | Cancer | Matching Normal Adjacent |
|---|---|---|---|
| Pro53P | Prostate 1-Normal | | 472.77 |
| Pro73P | Prostate 2-Normal | | 251.79 |
| Pro77P | Prostate 3-Normal | | 494.56 |
| ProC153 | Prostate 4-Normal | | 0.32 |
| Pro12B | Prostate 5-Cancer | 674.19 | 55.88 |
| Pro78XB | Prostate 6 | 109.53 | 55.54 |
| Pro84XB | Prostate 7 | 1770.5 | 522.96 |
| Pro109XB | Prostate 8 | 41.38 | 47.44 |
| Pro101XB | Prostate 9 | 1197.5 | 362.18 |
| Pro91X | Prostate 10 | 476.13 | 72.55 |
| Pro13XB | Prostate 11 | 3.28 | 15.96 |
| Pro125XB | Prostate 12 | 70.08 | 17.78 |
| Pro23B | Prostate 13 | 201.04 | 83.3 |
| Pro90XB | Prostate 14 | 424.38 | 849.41 |
| Pro588P | Prostate 15 | 120.28 | |
| Pro34B | Prostate 16 | 553.04 | 217.14 |
| Pro110 | Prostate 17 | 46.63 | 326.02 |
| Pro65XB | Prostate 18 | 639.72 | 2488.9 |
| Pro20XB | Prostate 19 | 61.18 | |
| Pro69XB | Prostate 20 | 30.48 | 4.26 |
| Pro326 | Prostate 21 | 59.53 | 10.38 |
| ProC215 | Prostate 22 | 525.68 | |
| ProC234 | Prostate 23 | 35.13 | |
| ProC280 | Prostate 24 | 1265.06 | |
| Pro10R | Prostate 25 (Prostatitis) | 81.71 | |
| Pro20R | Prostate 26 (Prostatitis) | 194.19 | |
| Pro258C | Prostate 27 (BPH) | 506.95 | |
| Pro263C | Prostate 28 (BPH) | 751.79 | |
| Pro267A | Prostate 29 (BPH) | 53.04 | |
| Pro271A | Prostate 30 (BPH) | 25.46 | |
| Pro460Z | Prostate 31 (BPH) | 102.48 | |
| ProC032 | Prostate 32 (BPH) | 353.51 | |
| Pro10P | Prostate 33 (BPH) | 287.71 | |
| Pro13P | Prostate 34 (BPH) | 19.93 | |
| Pro277P | Prostate 35 (BPH) | 209.54 | |
| Pro34P | Prostate 36 (BPH) | 59.47 | |
| Pro705P | Prostate 37 (BPH) | 13.74 | |
| Pro784P | Prostate 38 (BPH) | 22.05 | |
| Pro83P | Prostate 39 (BPH) | 57.45 | |
| Pro855P | Prostate 40 (BPH) | 392.31 | |
| ProC003P | Prostate 41 (BPH) | 0 | |
| ProC034P | Prostate 42 (BPH) | 6.71 | |
| Tst39X | Testis 1 | 1.87 | 0.19 |
| Kid106XD | Kidney 1 | 0 | 0 |
| Kid107XD | Kidney 2 | 0 | 0 |
| Kid109XD | Kidney 3 | 1.1 | 1.2 |
| Kid10XD | Kidney 4 | 0 | 0 |
| Kid11XD | Kidney 5 | 0 | 0 |
| Kid124XD | Kidney 6 | 0.6 | 0 |
| Kid126XD | Kidney 7 | 10.82 | 0.03 |
| Kid12XD | Kidney 8 | 0 | 8.02 |
| Bld32XK | Bladder 1 | 0 | 0 |
| Bld46XK | Bladder 2 | 1.9 | 0.9 |
| Bld66X | Bladder 3 | 0 | 0 |
| BldTR14 | Bladder 4 | 0.27 | 0 |
| BldTR17 | Bladder 5 | 0.69 | 0 |
| Lng47XQ | Lung 1 | 2.1 | 0 |
| Lng60XL | Lung 2 | 0.5 | 0 |
| Lng75XC | Lung 3 | 0 | 0 |
| Lng90X | Lung 4 | 0 | 0 |
| LngAC11 | Lung 5 | 0.81 | 0.42 |
| Liv15XA | Liver 1 | 2.5 | 10.9 |
| Liv174L | Liver 2 | 60 | 230.7 |
| Liv175L | Liver 3 | 144.7 | 52.3 |
| Liv187L | Liver 4 | 69.88 | 0.78 |
| Liv201L | Liver 5 | 26.31 | 53.9 |
| Liv390L | Liver 6 | 6.2 | 46.02 |
| Liv42X | Liver 7 | 2.73 | 32.36 |
| Pan71XL | Pancreas 1 | 0.12 | 0.1 |
| Pan77XL | Pancreas 2 | 138.99 | 162.06 |
| Pan82XP | Pancreas 3 | 0.41 | 0 |
| ClnAC19 | Colon 1 | 0.5 | 0.4 |
| ClnAS12 | Colon 2 | 0 | 0 |
| ClnAS43 | Colon 3 | 0 | 0 |
| ClnB34 | Colon 4 | 0.08 | 0 |
| ClnB56 | Colon 5 | 0 | 0 |
| ClnDC19 | Colon 6 | 0 | 0 |
| ClnRC01 | Colon 7 | 0 | 0 |
| Ovr1005 | Ovary 1 | 1.01 | |
| Ovr1028 | Ovary 2 | 1.12 | |
| Ovr1040 | Ovary 3 | 0.1 | |
| Ovr1050 | Ovary 4 | 5.12 | |
| Ovr18GA | Ovary 5 | | 0 |
| Ovr20GA | Ovary 6 | | 0 |
| Ovr230A | Ovary 7 | | 0 |
| Ovr233A | Ovary 8 | | 0 |
| Mam162X | Mammary Gland 1 | 0 | 0 |
| Mam14DN | Mammary Gland 2 | 0 | 0 |
| Mam19DN | Mammary Gland 3 | 0.36 | 0 |
| End10479 | Endometrium 1 | 4.4 | 0 |
| End12XA | Endometrium 2 | 2.5 | 0 |
| End28XA | Endometrium 3 | 0.4 | 0 |
| End3AX | Endometrium 4 | 0 | 0 |
| End5XA | Endometrium 5 | 0 | 0.5 |
| End65RA | Endometrium 6 | 0 | 0 |
| CvxKS52 | Cervix 1 | 0 | 0 |

TABLE 6-continued

Relative Levels of CSG Pro124 Expression in Individual Samples

| Sample ID | Tissue | Cancer | Matching Normal Adjacent |
|---|---|---|---|
| CvxKS83 | Cervix 2 | 0.12 | 0.94 |
| CvxNK23 | Cervix 3 | 0 | 0 |

0 = Negative

In the analysis of matching samples, the higher levels of expression were in prostate, showing a high degree of tissue specificity for prostate tissue. Of all the samples different than prostate analyzed, only liver tissue samples (liver 2 through liver 7) and pancreas tissue sample (pancreas 2) showed an expression comparable to the mRNA expression in prostate. All remaining tissue samples had relative Pro124 mRNA expression levels of less than 10 (except kidney cancer sample 7 that was 10.82). These results confirmed a high degree of tissue specificity as obtained with the panel of normal pooled samples (Table 5).

Furthermore, the level of mRNA expression in cancer samples and the isogenic normal adjacent tissue from the same individual were compared. This comparison provides an indication of specificity for the cancer (e.g. higher levels of mRNA expression in the cancer sample compared to the normal adjacent). Table 6 shows overexpression of Pro124 in 10 out of 15 primary prostate cancer tissues compared with their respective normal adjacent. Thus, there was overexpression in the cancer tissue for 66.66% of the prostate matching samples tested.

The mRNA overexpression in 66.66% of the prostate matching cancer samples tested is indicative of Pro124 being a diagnostic marker for prostate cancer.

What is claimed is:

1. A method for diagnosing the presence of prostate cancer in a patient comprising:
   (a) determining levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in cells, tissues or bodily fluids in a patient; and
   (b) comparing the determined levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3, with levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in cells, tissues or bodily fluids from a normal human control, wherein a change in determined levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in said patient versus normal human control is associated with the presence of prostate cancer.

2. A method of diagnosing metastases of prostate cancer in a patient comprising:
   (a) identifying a patient having prostate cancer that is not known to have metastasized;
   (b) determining levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in cells, tissues, or bodily fluid from said patient; and
   (c) comparing the determined levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 with levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in cells, tissue, or bodily fluid of a normal human control, wherein an increase in determined levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in the patient versus the normal human control is associated with a cancer which has metastasized.

3. A method of staging prostate cancer in a patient having prostate cancer comprising:
  (a) identifying a patient having prostate cancer;
  (b) determining levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in cells, tissue, or bodily fluid from said patient; and
  (c) comparing determined levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 with levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in cells, tissues, or bodily fluid of a normal human control, wherein an increase in determined levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in said patient versus the normal human control is associated with a cancer which is progressing and a decrease in the determined levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 is associated with a cancer which is regressing or in remission.

4. A method of monitoring prostate cancer in a patient for the onset of metastasis comprising:
  (a) identifying a patient having prostate that is not known to have metastasized;
  (b) periodically determining levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in cells, tissues, or bodily fluid from said patient; and
  (c) comparing the periodically determined levels with levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in cells, tissues, or bodily fluid of a normal human control, wherein an increase in any one of the periodically determined levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in the patient versus the normal human control is associated with a cancer which has metastasized.

5. A method of monitoring a change in stage of prostate cancer in a patient comprising:
  (a) identifying a patient having prostate cancer;
  (b) periodically determining levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in cells, tissues, or bodily fluid from said patient; and
  (c) comparing the periodically determined levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 with levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in cells, tissues, or bodily fluid of a normal human control, wherein an increase in any one of the periodically determined levels of polynucleotide comprising SEQ ID NO: 3, native protein expressed by the gene comprising polynucleotide comprising SEQ ID NO: 3, or native mRNA encoded by the gene comprising polynucleotide comprising SEQ ID NO: 3 in the patient versus the normal human control is associated with a cancer which is progressing in stage and a decrease is associated with a cancer which is regressing in stage or in remission.

\* \* \* \* \*